United States Patent [19]

Eckstein et al.

[11] 4,021,473
[45] May 3, 1977

[54] OPTICALLY ACTIVE N,N''-DIALKYL-N,N'-BIS(1-HYDROXYBUTYL-2-)ETHYLENEDIAMINE ESTERS AND THE SALTS THEREOF

[75] Inventors: Marian Eckstein; Jerzy May; Eleonora Herdegen; Daniel Kulig, all of Krakow, Poland

[73] Assignee: Krakowskie Zaklady Farmaceuticzne "Polfa", Krakow, Poland

[22] Filed: Oct. 22, 1974

[21] Appl. No.: 517,064

[52] U.S. Cl. .................... 260/473 R; 260/340.9; 260/474; 424/308
[51] Int. Cl.[2] .................................. C07C 69/76
[58] Field of Search .................. 260/473 R, 340.9

[56] References Cited
FOREIGN PATENTS OR APPLICATIONS 1,217,397   5/1966   Germany

OTHER PUBLICATIONS

Jenkins et al., "The Chemistry of Organic Medicinal Products," Wiley & Sons, Inc., N.Y., (1957), pp. 465–468.
Willianson et al., C.A. 57, 16400g, (1962).
Shepherd et al., C.A. 58, 13774f–13775g, (1963).
Societa Farmaceutics Italia, C.A. 75, 63110e, (1971).

*Primary Examiner*—Paul J. Killos

[57] ABSTRACT

New optically active esters of N,N'-dialkyl-N,N'-bis-(1-hydroxy-2-butyl)ethylenediamine and their salts, which shown antiarrhythmic, coronary and spasmolytic activity and a protective action in the case of myocardial infarcts corresponding to the formula:

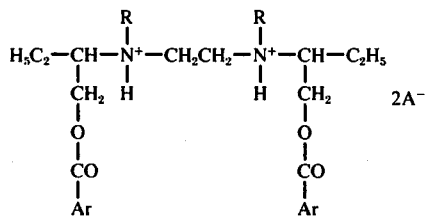

in which the R groups may be the same or different and R is a $C_nH_{2n+1}$ group wherein $n = 1-4$;

Ar denotes a phenyl group substituted in positions 3,4 by $-OCH_3$, $-OCH_2O-$ or $-OC_2H_5$ groups or in positions 3, 4, 5 by $-OCH_3$ or $-OC_2H_5$ groups;

A denotes the anion of a hydrohalic acid, sulfuric acid, and aryl or alkyl carboxylic or sulfonic acid, wherein the aryl group is phenyl, o-or p-tolyl, o-or p-hydroxyphenyl, o-or p-aminophenyl or naphthyl and the alkyl group has from 1 to 4 carbon atoms.

9 Claims, No Drawings

OPTICALLY ACTIVE N,N'''-DIALKYL-N,N'-BIS(1-HYDROXYBUTYL-2-)ETHYLENEDIAMINE ESTERS AND THE SALTS THEREOF

BACKGROUND OF THE INVENTION

The antituberculous action of DL- N,N'-dimethyl-N,N' -bis-(1-hydroxy-2-butyl)-ethylenediamine (J. med. pharm. Chem. 5,84 1962) is known.

SUMMARY OF THE INVENTION

The invention relates to new optically active N,N' -dialkyl-N,N'-bis-(1-hydroxy-2-butyl)-ethylenediamine esters and their pharmaceutically acceptable salts, of the formula 1:

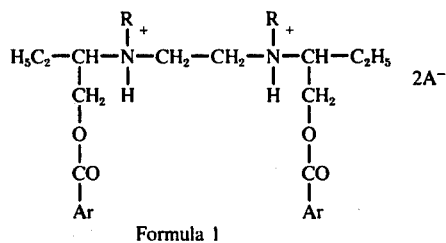

Formula 1 in which the R groups may be the same or different and R is a $C_nH_{2n+1}$ group wherein $n = 1-4$; Ar denotes a phenyl group substituted in positions 3, 4, by $-OCH_3$, $-OC_2H_5$ or $-O-CH_2-O-$ groups, or in positions 3, 4, 5 by $-OCH_3$ or $-OC_2H_5$ groups; A denotes the anion of a hydrohalic acid, sulfuric acid, an aryl or alkyl carboxylic or sulfonic acid, wherein the aryl group is phenyl, o- or p-tolyl, o- or p-hydroxyphenyl, o- or p-aminophenyl or naphthyl and the alkyl group has from 1 to 4 carbon atoms.

The compounds according to this invention show a marked action on the circulatory system.

A particularly strong antiarrhythmic activity and strong spasmolytic action upon the smooth muscles of blood vessels is shown by 3, 4, 5-trimethoxybenzoic acid esters.

Among them, a particularly strong antiarrhythmic activity and protective action in the case of cardiac infarcts is shown by N,N' -dimethyl-N,N' -bis-[1-(3',-4',5'-trimethoxybenzoyloxy-2-butyl)] -ethylenediamine and especially by the L (+) isomer and its salts. Some of these salts are levorotatory though their L configuration is retained.

DESCRIPTION OF PREFERRED EMBODIMENTS

The antiarrhythmic properties of the compounds of the invention were found in different experimental cardiac arrhythmias in rats induced by calcium or barium chloride, digoxin or adrenaline. The dose inhibiting the above mentioned arrhythmias in rats is about 250γ/kg whereas a similar or weaker action is shown by quinidine at a dose of 10 mg/kg, by propranolol at a dose of 1 mg/mg, by lignocaine at a dose of 1 mg/kg. A similar antiarrhythmic effect was observed in cats and in rabbits. In arrhythmias induced in cats by barium chloride or strophantin the L (+) N,N'-dimethyl-N,N'-bis-[1-(3',4',5'-trimethoxybenzoyloxy-2-butyl)]-ethylenediamine administered as the readily soluble dihydrochloride shows an activity 10-20 times stronger than the activity of quinidine or pronestyl [p-amino-N-(2-diethylaminoethyl)benzamide hydrochloride]. In rabbit arrhythmias induced by barium chloride, strophantin or aconitine, the L(+) N,N'-dimethyl-N,N'-bis-[1-(3',4',5'-trimethoxybenzoyloxy-2-butyl)]ethylenediamine dihydrochloride was about 10 times more active than quinidine or pronestyl. The compounds according to this invention considerably increase the blood supply to the cardiac muscle. Moreover they are strong spasmolytics and they inhibit the contraction induced by barium chloride, acetylcholine, histamine or serotonin of isolated organs at a concentration about 100 times lower than that of papaverine. The compounds have a wide therapeutic margin between the effective doses in the experiments described and the lethal doses. In experimental myocardial infarcts in dogs, L(+) N,N'-dimethyl-N,N'-bis-[1-(3',4',-5'=trimethoxybenzoyloxy-2-butyl)]ethylenediamine dihydrochloride protects even at a dose of 0.2 mg/kg against ventricular fibrillation and circulation breakdown i.e., against complication causing a sudden death in infarct cases.

The compounds obtained according to the invented method are therefore helpful in treating circulatory system diseases such as arrhythmias, myocardial infarcts, coronary disorders, angina pectoris and hypertension in humans and animals. A pharmacologic activity of this kind of the mentioned esters is unexpected in view of the prior art mentioned above. Consequently, the optically active esters form a new group of compounds exerting antiarrhythmic and protective action in case of myocardial infarcts.

Compounds according to this invention may be mixed with pharmaceutically harmless carriers such as talc, lactose, starch, ethyl cellulose, agar-pectin, stearic acid, magnesium stearate, sodium bicarbonate or gelatin.

For oral and parenteral administration, salts such as the di-p-toluenesulfonate or 5-sulfosalicylate, dihydrochloride dimaleate and others are used. These salts make it also possible to obtain stable aqueous solutions.

The solid and fluid preparations described above may be in the form of capsules, tablets, pills, powder, granules, suppositories, ampoules or drops.

Optically active N,N'-dialkyl-N,N'-bis-(1-hydroxy-2-butyl) ethylenediamine esters with 3,4-dialkoxy or 3',-4',5'-trialkoxybenzoic acids of the general formula 1 in which R, Ar, A have the meaning stated above, are obtainable by esterification of optically active N,N'-dialkyl-N,N'-bis-(1-hydroxy-2-butyl)-ethylenediamine with aromatic acids or their acid halides or esters of the general formula 2:

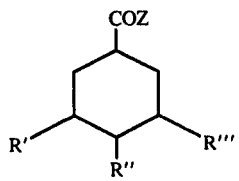

formula 2 in which R' denotes H and R'' = R''' and denotes $-OCH_3$ or $-OC_2H_5$ or R' denotes H and R'' and R''' denote $-OCH_2O-$, $OCH_3$, $-OC_2H_5$ or R' = R'' = R''' and denote $-OCH_3$ or $-OC_2H_5$, Z denotes OH, Cl, Br, $-OC_nH_{2n+1}$ wherein $n = 1, 2$ or 3 and the reaction product is converted in a known manner into optically active physiologically acceptable salts, for instance with mineral acids, alkyl or aryl carboxylic sulfonic acids.

If the esterification is carried out using chlorides or bromides of acids of formula 2, it is most advantageous to carry out the reaction at a molar ratio of 1 : 2.2–2.5 of the optically active ethylenediamine to the chlorides or bromides of acids of formula 2, in the presence of a tertiary amine such as pyridine, triethylamine, N-methylpiperidine and others, used in an amount equivalent to the chloride or bromide of the formula 2, in a medium of an inert solvent having a boiling point of 60°–140° C, such as dioxane, benzene, toluene and the like.

On the other hand, if esters of lower alcohols with acids of the the general formula 2 are used for the esterification, the reaction is conducted in the presence of small amounts of alkali metal alcoholates and the lower alcohol formed during the reaction is removed.

EXAMPLE I

To a vigorously stirred solution of 60 g (0.26 mole) of L (+) N,N'-dimethyl-N,N'-bis-(1-hydroxy-2-butyl)-ethylenediamine of about 99% purity, $[\alpha]_D^{20} = +24°$ ($C_2H_5OH$, $c = 5$), $n_D^{20} = 1.4718$, in 330 ml of anhydrous dioxane and 49 g of anhydrous pyridine or an equivalent amount of triethylamine, a solution of 143 g (0.62 mole) of 3,4,5-trimethoxybenzoyl chloride in 275 ml of anhydrous dioxane at a temperature of about 20° – 33° C is slowly added dropwise within about two hours. Then the reaction mixture is heated to a temperature of about 102° C and stirred at that temperature under reflux for 3 – 5 hours. The solvent is removed under reduced pressure and to the residue 1000 ml of ethyl acetate is added in portions and then 900 ml. of a saturated solution of $Na_2CO_3$ is added dropwise with stirring. Two layers are formed, and a white precipitate of a mixture of inorganic salts separated. The salts are filtered off, in the filtrate the layers are separated and the ethyl acetate layer is washed with water. Thereupon the solution is dried with anhydrous $Na_2SO_4$, the sulfate is separated and the filtered solution is evaporated to dryness under reduced pressure. The residue which is a crude ester base is dissolved in anhydrous ether and is saturated with dry gaseous hydrogen chloride at a temperature of about −5° C, with continuous stirring, to a pH value of about 2. After filtering off the precipitate and after washing with ether the L (+) N,N'-dimethyl-N,N'-bis-[1-(3',4',s'-trimethoxybenzoyloxy-2-butyl)]ethylenediamine dihydrochloride in a yield of 143 g is obtained.

L (+) N,N'-dimethyl-N,N'-bis-[1-(3',4',5'-trimethoxybenzoyloxy-2-butyl)]ethylenediamine dihydrochloride: $C_{32}H_{48}N_2O_{10} \cdot 2HCL$ (m. wt.:693.65) is a white crystalline powder having a melting point in the range of 83° to 113° C depending on the content of water and on the method of heating $[\alpha]_D^{20} = -7.0°$ to $-7.5°$ ($c = 5$, water) $[\alpha]_D^{20} = -6.4°$ ($c=2.5$, ethanol). The dihydrochloride forms mono-, di-, and trihydrates depending on the conditions of drying. When air-dried, the trihydrate is obtained; when vacuumdried at a temperature of 60° C, the monohydrate is formed; when dried without vacuum at a temperature of about 50° C, in most cases the dihydrate is obtained. The dihydrochloride is very soluble in water (about 50%), soluble in chloroform, ethanol, slightly soluble in methanol, weakly or insoluble in benzene, carbon tetrachloride and ether.

The pH-value of an 8% aqueous solution is about 2.20.

EXAMPLE II

To a vigorously stirred solution of 40 g (0.17 mole) of L (+) N,N'-dimethyl-N,N'-bis-(1-hydroxy-2-butyl) ethylenediamine and of 33 g of pyridine or of an equivalent amount of triethylamine in 220 ml of anhydrous benzene in apparatus protected against humidity, a solution of 95.3 g (0.41 mole) of 3',4',5'-trimethoxybenzoyl chloride in 184 ml of anhydrous benzene at a temperature of 25° – 30° C, was added drop by drop within a period of two hours. Then the solution was refluxed for 4 hours. From the reaction mass the solvent was distilled off in vacuo and the residue was treated with ethyl acetate and with a solution of $Na_2CO_3$ as stated in example I. From the dried solution in ethyl acetate the solvent was removed in vacuum to dryness, while the remaining dense mass was dissolved while stirring in 450 ml of anhydrous ether.

The solution was filtered from a small amount of undissolved solid and the ether was dissolved off from the filtrate. The residual crystalline crude ester base is converted into the dihydrochloride as stated in example I. L (+) N,N'-dimethyl-N,N' -bis-[1-(3',4',5'-trimethoxybenzoyloxy-2-butyl)]ethylenediamine dihydrochloride is obtained in a yield of 105 g (88%).

EXAMPLE III

To a cooled solution of 6 g of L (+) N,N'-dimethyl-N,N'-bis-[1-(3',4',5'-trimethoxybenzoyloxy-2-butyl)] ethylenediamine dihydrochloride in 80 ml of distilled water, a 10% ammonia solution is slowly added to a pH of about 10, with stirring. A white, initially stringy product separates but solidifies after cooling at a temperature of 0° C. A crystalline L (+) N,N'-dimethyl-N,N'-bis-[1-(3',4',5'-trimethoxybenzoyloxy-2-butyl)-]ethylenediamine base with a melting point of 60°–62° C; $[\alpha]_D^{20} = +24°$ ($c=5$, ethanol) is obtained in a yield of 4.89 g (89.4%).

EXAMPLE IV

Into a solution of 1 g of L (+) N,N'-dimethyl-N,N'-bis-[1-(3',4',5'-trimethoxybenzoyloxy-2-butyl)]ethylenediamine in 10 ml ethanol, a solution of 1.24 g of picric acid 74.2% in 15 ml of ethanol is added. The separated initially dense product solidifies quickly in the refrigerator. L (+) N,N'-dimethyl-N,N'-bis-[1-(3',-4',5'-trimethoxybenzoyloxy-2-butyl)]ethylenediamine dipicrate having a melting point of 198°–199° C is obtained in a yield of 1.6 g (91%).

EXAMPLE V

Into a solution of 1 g of L (+) N,N'-dimethyl-N,N'-bis-[1-(3',4',5'-trimethoxybenzoyloxy-2-butyl)]ethylenediamine in 10 ml of ethanol, a solution of 0.44 g of maleic acid in 4 ml of ethanol is dropped in. After cooling down to a temperature of −10° C a white dense oil which solidifies at a temperature of about 0° C, separates. The product is washed with cold ethanol and then dried.

L (+) N,N'-dimethyl-N,N'-bis-[1-(3',4',5'-trimethoxybenzoyloxy-2-butyl)]ethylenediamine dimaleate with a melting point of 128° – 129° C is obtained in a yield of 1.3 g (94%).

EXAMPLE VI

Into a solution of 1 g L (+) N,N'-dimethyl-N,N'-bis-[1-(3',4',5'-trimethoxybenzoyloxy-2-butyl)]ethylenediamine in 10 ml of ethanol a solution of 0.49 g of oxalic acid dihydrate in 10 ml of ethanol is added. After cooling in the refrigerator a white product precipitates, which after filtering off and washing was dried over $CaCl_2$.

The yield is 1.24 g (yield 94%) of L (+) N,N'-dimethyl-N,N'-bis-[1-(3',4',5'-trimethoxybenzoyloxy-2-butyl)]ethylenediamine dioxalate monohydrate with a melting point of 100°–102° C.

EXAMPLE VII

To a solution of 0.79 g of L (+) N,N'-dimethyl-N,N'-bis-[1-(3',4',5'-trimethoxybenzoyloxy-2-butyl)]ethylenediamine in 8 ml of ethanol a solution of 0.53 g of p-toluenesulfonic acid in 3 ml of ethanol is added dropwise.

The product is separated after cooling to a temperature of about −10° C. 0.79 g of L (+) N,N'-dimethyl-N,N'-bis-[1-(3',4',5'-trimethoxybenzoyloxy-2-butyl)-]ethylenediamine di-p-toluenesulfonate having a melting point of 171°–172° C is obtained.

EXAMPLE VIII

Into a solution of 1 g L (+) N,N'-dimethyl-N,N'-bis-[1-(3',4',5'-trimethoxybenzoyloxy-2-butyl)]ethylenediamine in 10 ml of ethanol a solution of 0.98 g of 5-sulfosalicylic acid in 5 ml of ethanol was added. At a temperature of about −10° C colorless crystalline L (+) N,N'-dimethyl-N,N'-bis-[1-(3',4',5'-trimethoxybenzoyloxy-2-butyl)]ethylenediamine bis-5-sulfosalicylate separates in a yield of 1.42 g.

EXAMPLE IX

To a solution of 7 g (0.03 mole) of D (−) N,N'-dimethyl-N,N'-bis-(1-hydroxy-2-butyl)ethylenediamine of 99.4% purity, $[\alpha]_D^{20} = -24°$ (c=5, ethanol), in 39 ml of dry anhydrous dioxane and 5.8 g of anhydrous pyridine or an equivalent of triethylamine, a solution of 16.7 g (0.072 mole) of 3',4',5'-trimethoxybenzoylchloride in 32 ml of dry dioxane was added within an hour by stirring at a temperature of 22°–27° C. The mixture was refluxed and stirred for 4 hours.

The procedure of example I was continued. D (−) N,N'-dimethyl-N,N'-bis-[1-3',4',5'-trimethoxybenzoyloxy-2-butyl)]ethylenediamine dihydrochloride was isolated in a yield of 15.5 g (74%). After recrystallization from isopropanol it melted at 81°–83° C, $[\alpha]_D^{20} = +7°$.

EXAMPLE X

The stock solution having a pH of 2.8 – 2.9 was prepared by dissolving 10.0 g of L (+) N,N'-dimethyl-N,N'-bis-[1-(3',4',5'-trimethoxybenzoyloxy-2-butyl)-]ethylenediamine, m.p. 60°–62° C, $[\alpha]_D^{20} = +22.2°$, (c=5, ethanol), in 332.5 ml of 0.1 N HCl solution and twice distilled water for injection was added up to a volume of 1000 ml. Then the solution was filtered and sterilized at 120° for 20 minutes.

The stock solution for injection can be prepared by dissolving 10.26 g of L (+) N,N'-dimethyl-N,N'-bis-[1-(3',4',5'-trimethoxybenzoyloxy-2-butyl)]ethylenediamine dihydrochloride monohydrate in 500 ml of twice distilled water for injection, by filtration, then by filling up to 1000 ml with water and by sterilizing as given above.

The stock solution was poured into ampoules having a volume of 1 or 2 ml. For preparation of tablets and coated pills both containing 7.5 or 15 mg of active compound (calculated as a base), the calculated amount of dihydrochloride or dimaleate of the mentioned L (+) N,N'-dimethyl-N,N'-bis-[1-(3',4',5'-trimethoxybenzoyloxy-2-butyl)]ethylenediamine was used.

TABLE 1

Salts of L (+) N,N'-dimethyl-N,N'-bis[1-(3',4',5'-trimethoxybenzoyloxy-2-butyl)]ethylenediamine.

| Salt | Formula mol weight | melting point solvent for recrystallization | $[\alpha]_D^{20}$ |
|---|---|---|---|
| Dihydrochloride | $C_{32}H_{48}N_2O_{10}$ . 2 HCL 693.65 forms mono di and trihydrates | in the range of 83 – 113° C anhydrous ethanol | a) −7.5° (c=5,$H_2O$) b) − 6.4° (c=2.5, ethanol) c) −5.5° (c=5, pyridine) |
| Dipicrate | $C_{32}H_{48}N_2O_{10}$ . 2 $C_6H_3N_3O_7$ 1078.94 | 208 – 210° C acetone | + 4.0° (c=0.125, acetone) |
| Dimaleate | $C_{32}H_{48}N_2O_{10}$ . 2 $C_4H_4O_4$ 852.86 | 129– 131° C methanol | a) + 6.7° (c=1,$H_2O$) b) 8.9° (c=2,methanol) |
| Dioxalate | $C_{32}H_{48}N_2O_{10}$ . 2 $C_2H_2O_4$ 800.80 | 101 – 103° C acetone | + 8.0° (c=1,methanol) |
| Di p-toluenesulfonate | $C_{32}H_{48}N_2O_{10}$ . 2 $C_7H_9NSO_2$ 965.10 | 171 – 172° C anhydrous ethanol | − 2.5° C (c=1,methanol) |
| Di 5-sulfosalicylate | $C_{32}H_{48}N_2O_{10}$ . $C_7H_6SO_6.H_2O$ | 135 – 138° C (not clear) 141 – 145° C (fully clear) | − 1.75° (c=4,methanol) |

All compounds give correct elemental analyses (C,H,N) within ± 0.4% values calculated theoretically. The optical rotation was determined on an automatic polarimeter Polartronic I.

In the text, the term "propranolol" is the international non-proprietary name recommended by the World Health Organization for the betablocking agent (±)-1-isopropylamino-3-naphth-1'-yloxypropa-2-ol hydrochloride ($C_{16}H_{21}NO_2.HCl$).

We claim:
1. A salt of an optically active ester of N,N'-dialkyl-N,N'-(bis-1-hydroxy-2-butyl) ethylenediamine of the formula:

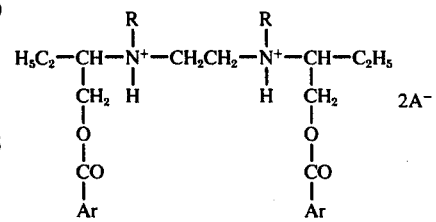

wherein the R groups may be the same or different and R denotes a $C_nH_{2n+1}$ group wherein n = 1–4;

Ar denotes a phenyl group which is substituted in positions 3,4 by —$OCH_3$, —$OC_2H_5$, or —$OCH_2O$— groups or in positions 3,4,5, by —$OCH_3$ or —$OC_2H_5$ groups; and A denotes the anion of a hydrohalic acid, sulfuric acid, an aryl or alkyl carboxylic or sulfonic acid, wherein the aryl group is phenyl o-or p-tolyl, o-or p-hydroxyphenyl, o-or p-aminophenyl or naphthyl and the alkyl group has from 1 to 4 carbon atoms.

2. L (+) N,N'-dimethyl-N,N'-bis-[1-(3',4',5'-trimethoxybenzoyloxy-2-butyl)]ethylenediamine dihydrochloride.

3. L (+) N,N'-dimethyl-N,N'-bis[1-(3',4',5'-trimethoxybenzoyloxy-2-butyl)]ethylenediamine.

4. L (+) N,N'-dimethyl-N,N'-bis-[1-(3',4',5'-trimethoxybenzoyloxy-2-butyl)]ethylenediamine dipicrate.

5. L (+) N,N'-dimethyl-N,N'-bis-[1-(3',4',5'-trimethoxybenzoyloxy-2-butyl)]ethylenediamine dimaleate 6. L (+) N,N'-dimethyl-N,N'-bis-[1-(3',4',5'-trimethoxybenzoyloxy-2-butyl)]ethylenediamine dioxalate 7. L (+) N,N'-dimethyl-N,N'-bis-[1-(3',4',5'-trimethoxybenzoyloxy-2-butyl)]ethylenediamine di(p-toluenesulfonate)

8. L (+) N,N'-dimethyl-N,N'-bis-[1-(3',4',5'-trimethoxybenzoyloxy-2-butyl)]ethylenediamine di(5-sulfosalicylate)

9. D (−) N,N'-dimethyl-N,N'-bis-[1-(3',4',5'-trimethoxybenzoyloxy-2-butyl)]ethylenediamine dihydrochloride

* * * * *